United States Patent
Baerends

(10) Patent No.: US 7,935,867 B2
(45) Date of Patent: May 3, 2011

(54) SPINACH LINE SSB66-1087F

(75) Inventor: Bernardus Baerends, Veenendaal (NL)

(73) Assignee: Seminis Vegetable Seeds, Inc., Woodland, CA (US)

(*) Notice: Subject to any disclaimer, the term of this patent is extended or adjusted under 35 U.S.C. 154(b) by 247 days.

(21) Appl. No.: 12/181,825

(22) Filed: Jul. 29, 2008

(65) Prior Publication Data

US 2010/0031382 A1 Feb. 4, 2010

(51) Int. Cl.
*A01H 1/00* (2006.01)
*C07H 21/04* (2006.01)
*C07K 14/415* (2006.01)
*C12N 15/00* (2006.01)

(52) U.S. Cl. ........ 800/295; 435/412; 435/418; 435/468; 536/23.1; 800/260; 800/278

(58) Field of Classification Search ........................... None
See application file for complete search history.

(56) References Cited

OTHER PUBLICATIONS

U.S. Appl. No. 12/130,856, filed May 30, 2008, Baerends.
U.S. Appl. No. 12/130,865, filed May 30, 2008, Baerends.
U.S. Appl. No. 12/130,871, filed May 30, 2008, Baerends.
U.S. Appl. No. 12/130,873, filed May 30, 2008, Baerends.
U.S. Appl. No. 12/181,813, filed Jul. 29, 2008, Baerends.
U.S. Appl. No. 12/181,826, filed Jul. 29, 2008, Baerends.
U.S. Appl. No. 12/181,833, filed Jul. 29, 2008, Baerends.
U.S. Appl. No. 12/181,839, filed Jul. 29, 2008, Baerends.
Application for European Union Community Plant Variety Right for Spinach Variety (*Spinacia oleracea* L.) SSB 66-1042, dated Feb. 3, 2005.
Application for European Union Community Plant Variety Right for Spinach Variety (*Spinacia oleracea* L.) SSB 66-1087F, filed Aug. 27, 2008.
U.S. Application for Plant Variety Protection for Spinach Variety (*Spinacia oleracea* L.) SSB 66-1087F, filed Oct. 31, 2008.
Zhang et al., An efficient agrobacterium tumefaciens-mediated transformation and regeneration system for cotyledons of spinach (*Spinacia oleracea*L.), *Plant Cell Reports*, 18:640-645, 1993.

*Primary Examiner* — Medina A Ibrahim
*Assistant Examiner* — Li Zheng
(74) *Attorney, Agent, or Firm* — Alissa Eagle, Esq.; SNR Denton US LLP

(57) ABSTRACT

The invention provides seed and plants of the spinach line designated SSB66-1087F. The invention thus relates to the plants, seeds and tissue cultures of spinach line SSB66-1087F, and to methods for producing a spinach plant produced by crossing a plant of spinach line SSB66-1087F with itself or with another spinach plant, such as a plant of another line. The invention further relates to seeds and plants produced by such crossing. The invention further relates to parts of a plant of spinach line SSB66-1087F, including the fruit and gametes of such plants.

24 Claims, No Drawings

SPINACH LINE SSB66-1087F

FIELD OF THE INVENTION

The present invention relates to the field of plant breeding and, more specifically, to the development of spinach line SSB66-1087F.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is spinach. Spinach (*Spinacia oleracea*) is a flowering plant in the family Amaranthaceae native to central and southwestern Asia. Spinach is now grown in many temperate parts of the world, but is most productive in cool seasons and climates as heat will cause spinach to bolt. It is an annual plant (rarely biennial) having flowers that mature into a small hard dry lumpy fruit cluster about 5-10 mm across containing several seeds.

Spinach has two stages in its life cycle including the vegetative, rosette stage in which the plant is marketable (about 35-40 days) and the bolting, seed stalk stage in which the plant is no longer marketable. Spinach can grow in a range of soils as long as they are moist and fertile, and particularly sandy loams that are high in organic matter. However, the plants typically do poorly in acid soil, which should be at least a pH of 6.0, having an optimum pH of 6.2-6.9.

Spinach performs poorly against weeds. For weed control, usually 2-4 cultivations are conducted in spinach fields, but fields should be shallow as to not harm any of the roots. Spinach also has a shallow root system, so spinach grows best in uniformly moist conditions. Fields are irrigated by either flooding, furrow, or overhead sprinklers, furrow or flooding irrigation is preferred because overhead irrigation can reduce yields by increasing the risk and levels of disease that thrive in moist, humid conditions.

Spinach is traditionally classified by sowing time (spring, summer, and winter spinach) and harvesting method. Spinach is considered to be dioecious, although there is a continuous range of monoecious types regarding the proportion of pistillate to staminate flowers per plant. In 1954, Janick and Stevenson (1954) reported a study of progeny segregation from selected crosses involving pistillate, staminate, and monoecious types to clarify the genetic mechanisms that bring about the monoecious complex in spinach. Sex determination in dioecious strains of spinach is controlled by a mechanism that acts as if it were a single factor pair; the pistillate plant is homozygous (XX), and the staminate plant is heterozygous (XY). The monoecious character in spinach appears to be controlled by one major gene, $X^m$, which was found to be allelic to the X Y factor pair. $X^m$ is incompletely dominant to X. The Y allele is dominant to X and $X^m$.

While breeding efforts to date have provided a number of useful spinach lines with beneficial traits, there remains a great need in the art for new lines with further improved traits. Such plants would benefit farmers and consumers alike by improving crop yields and/or quality.

SUMMARY OF THE INVENTION

In one aspect, the present invention provides a spinach plant of the line designated SSB66-1087F. Also provided are spinach plants having all the physiological and morphological characteristics of the spinach line designated SSB66-1087F. Parts of the spinach plant of the present invention are also provided, for example, including pollen, an ovule, a fruit, and a cell of the plant.

The invention also concerns seed of spinach line SSB66-1087F. The spinach seed of the invention may be provided as an essentially homogeneous population of spinach seed of the line designated SSB66-1087F. Essentially homogeneous populations of seed are generally free from substantial numbers of other seed. Therefore, seed of line SSB66-1087F may be defined as forming at least about 97% of the total seed, including at least about 98%, 99%, or more of the seed. The population of spinach seed may be particularly defined as being essentially free from hybrid seed. The seed population may be separately grown to provide an essentially homogeneous population of spinach plants designated SSB66-1087F.

In another aspect of the invention, a plant of spinach line SSB66-1087F comprising an added heritable trait is provided. The heritable trait may comprise a genetic locus that is a dominant or recessive allele. In one embodiment of the invention, a plant of spinach line SSB66-1087F is defined as comprising a single locus conversion. In specific embodiments of the invention, an added genetic locus confers one or more traits such as, for example, herbicide tolerance, insect resistance, disease resistance, and modified carbohydrate metabolism. The trait may be, for example, conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In another aspect of the invention, a tissue culture of regenerable cells of a plant of line SSB66-1087F is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line SSB66-1087F include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides spinach plants regenerated from a tissue culture of the invention, the plants having all the physiological and morphological characteristics of line SSB66-1087F.

In yet another aspect of the invention, processes are provided for producing spinach seeds, plants and fruit, which processes generally comprise crossing a first parent spinach plant with a second parent spinach plant, wherein at least one of the first or second parent spinach plants is a plant of the line designated SSB66-1087F. These processes may be further exemplified as processes for preparing hybrid spinach seed or plants, wherein a first spinach plant is crossed with a second spinach plant of a different, distinct line to provide a hybrid that has, as one of its parents, the spinach plant line SSB66-1087F. In these processes, crossing will result in the production of seed. The seed production occurs regardless of whether the seed is collected or not.

In one embodiment of the invention, the first step in "crossing" comprises planting seeds of a first and second parent spinach plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent spinach plants into plants that bear flowers. A third step may comprise preventing self-pollination of the plants, such as by emasculating the male portions of flowers, (i.e., treating or manipulating the flowers to produce an emasculated parent spinach plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent spinach plants. Yet another step comprises harvesting the seeds from at least one of the parent spinach plants. The harvested seed can be grown to produce a spinach plant or hybrid spinach plant.

The present invention also provides the spinach seeds and plants produced by a process that comprises crossing a first parent spinach plant with a second parent spinach plant, wherein at least one of the first or second parent spinach plants is a plant of the line designated SSB66-1087F. In one embodiment of the invention, spinach seed and plants produced by the process are first generation ($F_1$) hybrid spinach seed and plants produced by crossing a plant in accordance with the invention with another, distinct plant. The present invention further contemplates plant parts of such an $F_1$ hybrid spinach plant, and methods of use thereof. Therefore, certain exemplary embodiments of the invention provide an $F_1$ hybrid spinach plant and seed thereof.

In still yet another aspect of the invention, the genetic complement of the spinach plant line designated SSB66-1087F is provided. The phrase "genetic complement" is used to refer to the aggregate of nucleotide sequences, the expression of which sequences defines the phenotype of, in the present case, a spinach plant, or a cell or tissue of that plant. A genetic complement thus represents the genetic makeup of a cell, tissue or plant, and a hybrid genetic complement represents the genetic make up of a hybrid cell, tissue or plant. The invention thus provides spinach plant cells that have a genetic complement in accordance with the spinach plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line SSB66-1087F could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by spinach plant cells, tissues, plants, and seeds, formed by the combination of a haploid genetic complement of a spinach plant of the invention with a haploid genetic complement of a second spinach plant, preferably, another, distinct spinach plant. In another aspect, the present invention provides a spinach plant regenerated from a tissue culture that comprises a hybrid genetic complement of this invention.

In still yet another aspect, the invention provides a plant of an inbred spinach line that exhibits a combination of traits including one or more of slow bolting, slow growing, medium green/glossy leaf color, spineless seeds (smooth), a very high proportion of female plants, round leaf tip, ovate leaf shape, a semi-erect growth habit, and a resistance to downy mildew (=Peronospora farinosa f.sp. spinaciae (Pfs)) races Pfs 1 till Pfs 10. In certain embodiments, the combination of traits may be defined as controlled by genetic means for the expression of the combination of traits found in spinach line SSB66-1087F.

In still yet another aspect, the invention provides a method of determining the genotype of a plant of spinach line SSB66-1087F comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line SSB66-1087F, the method comprising the steps of: (a) preparing a progeny plant derived from line SSB66-1087F, wherein said preparing comprises crossing a plant of the line SSB66-1087F with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SSB66-1087F. The plant derived from line SSB66-1087F may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SSB66-1087F is obtained which possesses some of the desirable traits of the line as well as potentially other selected traits.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of spinach line SSB66-1087F. This line shows uniformity and stability within the limits of environmental influence for the traits described hereinafter. Spinach line SSB66-1087F provides sufficient seed yield. By crossing with a distinct second plant, uniform F1 hybrid progeny can be obtained.

A. Origin and Breeding History of Spinach Line SSB66-1087F

Spinach line SSB66-1087F was developed by pedigree selection from the LAZIO hybrid line. The origin and selections that led to the development of line SSB-1087F can be summarized as follows (S=Selfing, M=Mass selection):

| Year 1 | F2 generation grown from LAZIO. Selected for Pfs 10 resistance. |
|---|---|
| Year 2 | F2.S1 generation grown. Selected for Pfs 10 resistance, color and leaf shape. |
| Year 3 | F2.S2 generation grown. Selected for Pfs 10 resistance, color and leaf shape. |
| Year 4 | F2.S2.M1 generation grown. Selected for uniformity. |

Observations during mass selection one year and stock seed production in another year confirm that SSB66-1087F is uniform and stable. As is true with other spinach varieties, a small percentage of off-types can occur for almost any characteristics during the course of repeated multiplications. However, no variants were observed during the two years in which SSB66-1087F was observed to be uniform and stable.

B. Physiological and Morphological Characteristics of Spinach Line SSB66-1087F

In accordance with one aspect of the present invention, there is provided a plant having the physiological and morphological characteristics of spinach line SSB66-1087F. A description of the physiological and morphological characteristics of spinach line SSB66-1087F is presented in Table 1.

TABLE 1

Physiological and Morphological Characteristics of Line SSB66-1087F and a Selected Variety

| CHARACTERISTIC | SSB66-1087F | SSB66-1042F |
|---|---|---|
| Species | *Spinacia oleracea* L. | *Spinacia oleracea* L. |
| Ploidy | Diploid | Diploid |
| Maturity | | |
| Growth Rate | Slow (Norgreen) | Slow (Norgreen) |
| Days from planting to prime market stage | 111 | 81 |
| Plant (Prime Market Stage) | | |
| Habit | Semi-erect (Long Standing Bloomsdale) | Flat (Viroflay) |
| Size | Medium | Small (America) |
| Spread (cm) | 14.4 | 11.8 |
| Height (cm) | 4.9 | 3.4 |
| Seedling Cotyledon | | |
| Width (mm) | 5.0 | 5.3 |
| Length (mm) | 54.2 | 54.3 |
| Tip | Rounded | Rounded |
| Color | Medium Green | Medium Green |
| Color Chart Name | RHS | RHS |
| Color Chart Value | 143B | 144A |
| Leaf (First Foliage Leaves) | | |
| Shape | Ovate | Ovate (Broad Ovate) |
| Base | V-shape | V-shape |
| Tip | Round | Round |
| Margin | Flat | Slightly Curled |
| Upper Surface Color | Dark Green (Long Standing Bloomsdale) | Dark Green (Long Standing Bloomsdale) |
| Color Chart Name | RHS | RHS |
| Color Chart Value | 137A | 137A |
| Lower Surface Color (Compared with upper surface) | Lighter | Lighter |
| Color Chart Name | RHS | RHS |
| Color Chart Value | 137B | 137B |
| Leaf (Prime Market Stage) | | |
| Surface | Smooth (Viroflay) | Smooth (Viroflay) |
| Shape | Elliptic (broad elliptic) | Ovate |

TABLE 1-continued

Physiological and Morphological Characteristics of Line SSB66-1087F and a Selected Variety

| CHARACTERISTIC | SSB66-1087F | SSB66-1042F |
|---|---|---|
| Base | Straight | Lobed |
| Tip | Round | Round-pointed |
| Margin | Curled Under | Curled Under |
| Upper Surface Color | Medium Green (Giant Nobel) | Dark Green (Standing Bloomsdale) |
| Color Chart Name | RHS | RHS |
| Color Chart Value | 137A | 139A |
| Lower Surface Color (Compared with upper surface) | Lighter | Lighter |
| Color Chart Name | RHS | RHS |
| Color Chart Value | 137C | 137C |
| Luster | Glossy | Dull |
| Blade Size | Small (Long Standing Bloomsdale) | Small (Long Standing Bloomsdale) |
| Blade Lobing | Lobed (Weak) | Lobed (Weak) |
| Petiole Color | Medium Green | Medium Green |
| Color Chart Name | RHS | RHS |
| Color Chart Value | 137C | 137B |
| Petiole Red Pigmentation | Absent | Absent |
| Petiole Length to the Blade (cm) | 3.8 | 3.7 |
| Petiole Length | Medium | Short |
| Petiole Diameter (mm) | 3.2 | 2.9 |
| Petiole Diameter | Medium | Small |
| Seed Stalk Development | | |
| Start of Bolting (10% of plants) | Late (Norgreen) | Late (Norgreen) |
| Height of Stalk (cm) | 97.9 | 86.4 |
| Leaves on Stalk of Female Plant | Few or None | Few or None (few) |
| Leaves on Stalk of Male Plant | | |
| Plants that are Female | 91-100% | 91-100% |
| Plants that are Male | 0% | 0% |
| Plants that are Monoecious | 0-10% | 0-10% |
| Seed | | |
| Surface | Smooth | Smooth |
| Disease Reaction | | |
| Downy Mildew (*Peronospora spinaciae*) Race 1 | Resistant | Resistant |
| Downy Mildew (*Peronospora spinaciae*) Race 2 | Resistant | Resistant |
| Downy Mildew (*Peronospora spinaciae*) Race 3 | Resistant | Resistant |
| *Fusarium* Wilt (*Fusarium oxysporum f.* sp. *spinaciae*) | Not Tested | Not Tested |
| White Rust (*Albugo Occidentalis*) | Not Tested | Not Tested |
| Curly Top Virus | Not Tested | Not Tested |
| Cucumber Mosaic Virus | Susceptible | Susceptible |
| Other - Down Mildew Race 4, 5-10 | Resistant 4, 5-10 | Susceptible 5-10 |

*These are typical values. Values may vary due to environment. Other values that are substantially equivalent are also within the scope of the invention.

Line SSB66-1087F has been self-pollinated and planted for a number of generations to produce the homozygosity and phenotypic stability to make this line useful in commercial seed production. No variant traits have been observed or are expected for this line. Spinach line SSB66-1087F, being substantially homozygous, can be reproduced by planting seeds of the line, growing the resulting spinach plant under self-pollinating or sib-pollinating conditions and harvesting the resulting seeds using techniques familiar to one of skill in the art.

C. Breeding Spinach Line SSB66-1087F

One aspect of the current invention concerns methods for crossing the spinach line SSB66-1087F with itself or a second plant and the seeds and plants produced by such methods. These methods can be used for propagation of line SSB66-1087F, or can be used to produce hybrid spinach seeds and the plants grown therefrom. Hybrid seeds are produced by crossing line SSB66-1087F with second spinach parent line.

The development of new varieties using one or more starting varieties is well known in the art. In accordance with the invention, novel varieties may be created by crossing line SSB66-1087F followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SSB66-1087F for the purpose of developing novel spinach lines, it will typically be preferred to choose those plants which either themselves exhibit one or more selected desirable characteristics or which exhibit the desired characteristic(s) when in hybrid combination. Examples of desirable characteristics may include, but are not limited to, resistance to one or more viruses (such as cucumber mosaic virus, Beet western yellows virus, and Beet curly top virus, for example), one or more fungi (such as white rust, blue mold, downy mildew, Fusarium wilt, damping off disease caused by *Pythium*, and sclerotinia, for example), one or more bacteria (such as corky root rot and Bacterial Soft rot, for example), and one or more insects (green peach aphid, spinach leafminer (*Pegomyia hyoscyami*), Budworm injury (*Hylemya cilicrura*), cucumber beetle, silverleaf whitefly, Cabbage looper, flea beetles, root maggots and cutworms); or increased phenolic content to increase antioxidant capacity (Howard et al., 2002), for example.

Non-limiting examples of genes that may be utilized for generating transgenic spinach include RARI disease resistance proteins, as described in, for example, U.S. Pat. No. 7,098,378, the ability to tolerate high salt conditions, as described in, for example, U.S. Pat. Nos. 7,041,875 or 6,936,750; trehalose synthase for increased amounts of trehalose to increase tolerance to a variety of stresses, in particular to decreased availability of water, as described in, for example, U.S. Pat. No. 5,792,921; overexpression of phytochrome, such as for increased shade tolerance and/or darker green color, as described in, for example, U.S. Pat. No. 5,268,526; expression of reversibly glycosylated protein (RGP) for at least altered growth rates, as described in, for example, U.S. Pat. No. 6,194,638; improved growth under low-light conditions, such as with COP1, as described in, for example, U.S. Pat. No. 7,081,363 and so forth.

D. Performance Characteristics

As described above, line SSB66-1087F exhibits desirable agronomic traits, including slow bolting, longer seed stalks, and resistance to Pfs races 5 through 10. These and other performance characteristics of the line were the subject of an objective analysis of the performance traits of the line relative to other lines. The results of such an analysis are presented below.

TABLE 2

Performance Characteristics For Line SSB66-1087F

| LINE | Bolting | | | Seed Stalk | DM Resistance |
| | Y1 | Y2 | Y3 | Y3 | Pfs races |
| --- | --- | --- | --- | --- | --- |
| SSB66-1042F | 79 | 78 | 77 | 86.4 | Pfs 1, 2, 3, 4 |
| SSB66-1087F | 76 | 72 | 71 | 97.9 | Pfs 1, 2, 3, 4, 5, 6, 7, 8, 9, 10 |

Bolting = number of days after sowing
Seed Stalk = cm height of stalk
DM resistance = downy mildew resistance = *Peronospora farinosa* f. sp. *spinaciae*(Pfs) resistance E. Further Embodiments of the Invention In certain embodiments of the invention, plants are provided modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those spinach plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental spinach plant which contributes the locus for the desired characteristic is termed the nonrecurrent or donor parent. This terminology refers to the fact that the nonrecurrent parent is used one time in the backcross protocol and therefore does not recur. The parental spinach plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a spinach plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny diploid spinach plants of a backcross in which SSB66-1087F is the recurrent parent comprise (i) the desired trait from the non-recurrent parent and (ii) all of the physiological and morphological characteristics of diploid spinach line SSB66-1087F as determined at the 5% significance level when grown in the same environmental conditions.

Spinach varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of spinach plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of spinach are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Spinach Line SSB66-1087F by Genetic Engineering

Many useful traits that can be introduced by backcrossing, as well as directly into a plant, are those which are introduced by genetic transformation techniques. Genetic transformation may therefore be used to insert a selected transgene into the spinach line of the invention or may, alternatively, be used for the preparation of transgenes which can be introduced by backcrossing. Methods for the transformation of plants, including spinach, are well known to those of skill in the art. Techniques which may be employed for the genetic transformation of spinach include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Production of transgenic spinach plants, including at least *Spinacia oleracea* L., have been established. An exemplary protocol for transforming transgenic spinach is described by Zhang and Zeevaart (1999), in which cotyledon explants were infected with *Agrobacterium tumefaciens* strain LBA4404 carrying an exemplary selectable marker gene and reporter gene.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target spinach cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for spinach plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunI, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the spinach lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a spinach plant according to the invention. Non-limiting examples of particular genes and corresponding phenotypes one may choose to introduce into a spinach plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Spinach End Uses and Products

Spinach has many well known end uses, any one of which may be used in connection with a plant of the invention. Spinach is marketed to consumers in forms that include fresh or frozen single vegetables or mixtures of vegetables, and components of various pre-prepared and/or pre-packaged items. Common examples include, but are not limited to, pre-washed, bagged spinach marketed for use in salads, alone or mixed with other greens. Spinach may also be provided to consumers in forms that can be conveniently stored, such as frozen or canned single-servings, single- or mixed-vegetable packages designed for use in cooking, and others. Spinach has a high nutritional value and thus the plants and plant parts provided by the invention will also find beneficial use as an ingredient in various food products.

Therefore, in certain aspects of the invention, a food products is provided comprising a plant according to the invention or any part thereof. Methods for the production of such products are also provided. In specific embodiments of the invention, a product is provided or a method for the manufacture thereof, wherein the product is defined as comprising leaf tissue from a plant provided herein.

H. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a spinach variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a spinach plant by transformation.

Triploid: A cell or organism having three sets of chromosomes.

I. Deposit Information

A deposit of spinach line SSB66-1087F, disclosed above and recited in the claims, has been made with the American Type Culture Collection (ATCC), 10801 University Blvd., Manassas, Va. 20110-2209. The date of deposit was May 5, 2008. Upon issuance of a patent, all restrictions upon the deposit will be removed, and the deposit is intended to meet all of the requirements of 37 C.F.R. §1.801-1.809. The accession number for those deposited seeds of spinach line SSB66-1087F is ATCC Accession No. PTA-9186. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,268,526
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,792,921
U.S. Pat. No. 5,880,275
U.S. Pat. No. 6,194,638
U.S. Pat. No. 6,936,750
U.S. Pat. No. 7,041,875
U.S. Pat. No. 7,081,363
U.S. Pat. No. 7,098,378
An et al., *Plant Physiol.*, 88:547, 1988.
Bird et al., *Biotech. Gen. Engin. Rev.*, 9:207, 1991.
Bragdo, *Euphytica.*, 11(2):143-148, 1962.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125,1997

Howard et al., *J. Agric. Food Chem.*, 50 (21):5891-5896, 2002.
Janick and Stevenson, *Proc. Am. Soc. Hort. Sci.*, 63:444-146, 1954.
Khattak et al. *Euphytica*, 148(3):311-318, 2006.
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schemthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248
Zhang and Zeevaart, *Plant Cell Rep.*, 18:7-8, 1999.

What is claimed is:

1. A seed of spinach line SSB66-1087F, a sample of seed of said line having been deposited under ATCC Accession Number PTA-9186.

2. A plant grown from the seed of claim 1.

3. A plant part of the plant of claim 2.

4. The plant part of claim 3, wherein said part is selected from the group consisting of a seed, pollen, an ovule, a leaf, and a cell.

5. A spinach plant, or a part thereof, having all the physiological and morphological characteristics of the spinach plant of claim 2.

6. A tissue culture of regenerable cells of spinach line SSB66-1087F, a sample of seed of said line having been deposited under ATCC Accession Number PTA-9186.

7. The tissue culture according to claim 6, comprising cells or protoplasts from a plant part selected from the group consisting of embryos, meristems, cotyledons, pollen, leaves, anthers, roots, root tips, shoots, pistil, flower, seed and stalks.

8. A spinach plant regenerated from the tissue culture of claim 6, wherein the regenerated plant expresses all of the physiological and morphological characteristics of spinach line SSB66-1087F, a sample of seed of said line having been deposited under ATCC Accession Number PTA-9186.

9. A method of producing seed, comprising crossing the plant of claim 2 with itself or a second spinach plant and allowing seed to form.

10. The method of claim 9, comprising crossing the plant of spinach line SSB66-1087F with a spinach plant of a different genotype relative to said line.

11. An F1 hybrid seed produced by the method of claim 10.

12. An F1 hybrid plant produced by growing the seed of claim 11.

13. A method for producing a seed of a line SSB66-1087F-derived spinach plant comprising the steps of:
  (a) crossing a spinach plant of line SSB66-1087F, a sample of seed of said line having been deposited under ATCC Accession Number PTA-9186, with a second spinach plant; and
  (b) allowing seed of a SSB66-1087F-derived spinach plant to form.

14. The method of claim 13, further comprising the steps of:
  (c) crossing a plant grown from said SSB66-1087F-derived spinach seed with itself or a second spinach plant to yield additional SSB66-1087F-derived spinach seed;
  (d) growing said additional SSB66-1087F-derived spinach seed of step (c) to yield additional SSB66-1087F-derived spinach plants; and
  (e) repeating the crossing and growing steps of (c) and (d) to generate further SSB66-1087F-derived spinach plants.

15. A method of vegetatively propagating a plant of spinach line SSB66-1087F comprising the steps of:
  (a) collecting tissue capable of being propagated from a plant of spinach line SSB66-1087F, a sample of seed of said line having been deposited under ATCC Accession Number PTA-9186;
  (b) cultivating said tissue to obtain proliferated shoots; and
  (c) rooting said proliferated shoots to obtain rooted plantlets.

16. The method of claim 15, further comprising growing plants from said rooted plantlets.

17. A method of introducing a desired trait into spinach line SSB66-1087F comprising:
  (a) crossing a plant of line SSB66-1087F, a sample of seed of said line having been deposited under ATCC Accession Number PTA-9186, with a second spinach plant that comprises a desired trait to produce F1 progeny;
  (b) selecting an F1 progeny that comprises the desired trait;
  (c) crossing the selected F1 progeny with a plant of line SSB66-1087F to produce backcross progeny;
  (d) selecting backcross progeny comprising the desired trait and the physiological and morphological characteristic of spinach line SSB66-1087F; and
  (e) repeating steps (c) and (d) three or more times in succession to produce selected fourth or higher backcross progeny that comprise the desired trait.

18. A spinach plant produced by the method of claim 17, wherein the spinach plant comprises essentially all of the physiological and morphological characteristics of spinach line SSB66-1087F, a sample of seed of said line having been deposited under ATCC Accession Number PTA-9186.

19. A method of producing a plant of spinach line SSB66-1087F, a sample of seed of said line having been deposited under ATCC Accession Number PTA-9186, comprising an added desired trait, the method comprising introducing a transgene conferring the desired trait into a plant of spinach line SSB66-1087F to produce a plant of spinach line SSB66-1087F comprising an added desired trait.

20. A progeny plant of the plant of claim 2 that comprises all of the physiological and morphological characteristics of spinach line SSB66-1087F, a sample of seed of said line having been deposited under ATCC Accession Number PTA-9186.

21. A seed that produces the plant of claim 20.

22. A method of determining the genotype of the plant of claim 2, comprising obtaining a sample of nucleic acids from said plant and detecting in said nucleic acids a plurality of polymorphisms.

23. The method of claim 22, further comprising the step of storing the results of the step of detecting the plurality of polymorphisms on a computer readable medium.

24. A method of producing spinach comprising:
  (a) obtaining the plant of claim 2, and
  (b) collecting leaf tissue from the plant.

* * * * *